| United States Patent [19] | [11] | 4,010,087 |
|---|---|---|
| Wood et al. | [45] | Mar. 1, 1977 |

[54] PROCESS FOR PREPARING 3-PHENOXYBENZYL BROMIDE

[75] Inventors: Derek A. Wood, Sittingbourne; Ronald F. Mason, near Ashford, both of England

[73] Assignee: Shell Oil Company, Houston, Tex.

[22] Filed: Mar. 11, 1976

[21] Appl. No.: 665,991

[52] U.S. Cl. ............................................ 204/158 HA
[51] Int. Cl.$^2$ ............................................ B01J 1/10
[58] Field of Search ............................ 204/158 HA

[56] References Cited

UNITED STATES PATENTS

| 3,190,825 | 6/1965 | Huyser .................. 204/158 HA |
| 3,297,556 | 1/1967 | Boudakian et al. ......... 204/158 HA |

*Primary Examiner*—Howard S. Williams

[57] ABSTRACT

3-phenoxybenzyl bromide is prepared by treating 3-phenoxytoluene with bromine in the presence of ultraviolet radiation, at a temperature in the range of from 180° C to 250° C.

2 Claims, No Drawings

PROCESS FOR PREPARING 3-PHENOXYBENZYL BROMIDE

DESCRIPTION OF THE INVENTION

As is described in Belgian patent 809,867, 3-phenoxybenzyl bromide is of interest as a precursor for the preparation of insecticidal esters of certain cyclopropanecarboxylic acids.

The art shows that it is rather difficult to convert 3-phenoxytoluene to 3-phenoxybenzyl bromide. For example, the patent mentioned above describes the preparation of 3-phenoxybenzyl bromide by treating 3-phenoxytoluene with bromine in the presence of phosphorus trichloride, as catalyst, at a temperature above 220° C. The yield appear to be rather low — 60% — and substantial amounts of by-products, mainly the analogs wherein more than one of the hydrogen atoms of the methyl group has been replaced by bromine, and/or ring brominated analogs, tend to be formed. The direct product is not very suitable for preparation of the insecticides, because of the by-product content — removal of which is expensive and laborious. The low yield also is undesirable.

It now has been found that 3-phenoxybenzyl bromide can be prepared in very high yield, with high selectivity, by treating 3-phenoxytoluene with bromine in the presence of ultra-violet radiation at a temperature within the range of 180° C to 250° C. Preferably, a temperature within the range of from 200° C to 230° C is used. Best results are obtained when the reactants are brought together as close to the source of the radiation as is practicably possible.

The yield of 3-phenoxybenzyl bromide obtained by this process normally is above 85% and can be well over 95%. Only limited amounts of by-products — usually less than 10% and often less than 5% — are formed. Accordingly, the products obtained by this process usually can be used directly for the preparation of the insecticides. However, should it be considered desirable to have a purer product, removal of the by-products can be effected by methods known in the art.

The process of the invention can be carried out by using stoichiometric amounts of the two reactants. However, to minimize the formation of by-products, it is ordinarily desirable to employ a slight excess — of the order of 2-5 percent — of the 3-phenoxytoluene. For the same reason, it will usually be found desirable to add the bromine slowly to the thoroughly stirred 3-phenoxytoluene, to avoid local build-up of a high concentration of bromine, which would tend to promote further bromination.

Although the presence of an inert diluent in the reaction mixture is not known to be needed to obtain the high yields and selectivities provided by the process of the invention, such a diluent may be included in the reaction mixture. An excess of the 3-phenoxytoluene is suitable for this purpose and is most convenient, since it reduces the number of materials required, and facilitates recovery of the bromide product.

It has been found that high selective yields of the bromide are obtained when the treatment is conducted within the indicated range — i.e., 180°-250° C, preferably 200°-230° C. At temperatures below 180° C, a substantial amount of bromination of the phenyl ring occurs. Best results are obtained when the two reactants are pre-heated before mixing them.

The process according to the invention can be carried out batchwise, semi-continuously or continuously.

The ultra-violet radiation required can be provided by means known in the art. In order to optimize the yield of the 3-phenoxybenzyl bromide, it has been found that the distance between the ultra-violet radiation source and the reactants should be kept as short as possible. Good results have been obtained using a long small tube containing the ultra-violet radiation source placed in an oil bath heated to the required temperature, 3-phenoxytoluene and bromine being fed separately to the bottom of the tube through pipes which have been pre-heated to the required temperature.

If the reaction is carried out batchwise, bromine can be added gradually to a reaction vessel containing ultra-violet radiation 3-phenoxytoluene. If desired, an inert gas, such as nitrogen or helium, can be used as a carrier to facilitate the addition of the bromine.

When the process according to the present invention is carried out continuously, best results are obtained when bromine, if desired in the presence of an inert carrier gas such as nitrogen or helium, is introduced into the reactor just below the source of ultra-violet radiation, through a number of small openings in the end of the feedpipe which is preferably located perpendicular to the source of the radiation. Instead of the perforated end of the feedtube a sintered disc can be used as well. If desired, bromine can be added in stages or a number of reactors can be used, bromine being added in one or more of them.

Ordinarily, it will not be necessary to purify the product obtained; it is of sufficient quality to be used without further purification as a starting material in the preparation of the insecticides pesticides. If desired, however, the product can be purified, for instance by distillation or crystallization.

The invention is illustrated by means of the following Examples:

EXAMPLE I

A 100 ml batch reactor was fitted with an inlet pipe for bromine, a scrubber for the hydrogen bromide to be formed and an air-cooled ultra-violet radiation source (an Engelhard Hanovia lamp; medium pressure arc tube). The radiation source was placed in an inverted neck of the reactor which had openings in the upper part of the jacket above the source and which tapered below the source. The reactor was charged with 113 g of 3-phenoxytoluene and heated to 180° C. Then the theoretical amount of bromine (33 ml) was added over a 30-minute period, using nitrogen as a carrier, via a dip pipe ending in a glass sinter placed within the tapering part of the inverted neck. The product obtained was passed through the openings in the upper part of the inverted neck into the reactor contents. When the addition was complete the reaction mixture was allowed to cool. A sample of the reaction mixture was analysed using gas liquid chromatography (10% apiezon column). The conversion of 3-phenoxy toluene was quantitative, the yield of 3-phenoxybenzyl bromide was 85%, the remainder being ring brominated products.

EXAMPLE II

The experiment described in Example I was repeated at a temperature of 200° C. Again complete bromination had been obtained. The yield of 3-phenoxybenzyl bromide was 93%, only 7% ring brominated products had been formed.

EXAMPLE III

The experiment described in Example I was repeated at a reaction temperature of 220° C. Only 2% of ring brominated product had been formed. 3-phenoxybenzyl bromide was formed in 98% yield.

EXAMPLE IV

The experiment described in Example I was repeated at a temperature of 160° C. Under these circumstances, applying a temperature outside the range according to the present invention, no less than 30% ring brominated product was obtained.

EXAMPLE V

A continuous photobromination was carried out using the ultra-violet radiation source described in Example I. The source was placed within a glass beaker containing in the bottom two inlets for the reactants. The beaker was placed in an oil bath which was maintained at 225° C – 230° C. The upper part of the beaker was provided with a number of openings and surrounded by a glass compartment containing an upper outlet for hydrogen bromide formed during the reaction and a lower outlet for the product.

Over a period of 90 minutes 18.36 moles of 3-phenoxytoluene and 17.83 moles of bromine were pumped into the reactor, the internal reactor temperature being 220° C. The conversion was about 90%, almost no ring-brominated material could be detected in the product.

We claim:
1. A process for preparing 3-phenoxybenzyl bromide, which comprises treating 3-phenoxytoluene with bromine in the presence of ultra-violet radiation, at a temperature within the range of 180° C to 250° C.
2. A process according to claim 1 wherein the treatment is conducted at a temperature within the range of 200° C to 230° C.

* * * * *

UNITED STATES PATENT AND TRADEMARK OFFICE
CERTIFICATE OF CORRECTION

PATENT NO. : 4010087
DATED : March 1, 1977
INVENTOR(S) : Derek A. Wood and Ronald F. Mason It is certified that error appears in the above-identified patent and that said Letters Patent are hereby corrected as shown below:

In the left hand column, first page, between items "[21]" and "[52]", insert

-- [30] Foreign Application Data
March 24, 1975   United Kingdom...12133/75 --.

Signed and Sealed this

Tenth Day of May 1977

[SEAL]

Attest:

RUTH C. MASON
Attesting Officer

C. MARSHALL DANN
Commissioner of Patents and Trademarks